United States Patent [19]

Ishii et al.

[11] Patent Number: 4,554,255
[45] Date of Patent: Nov. 19, 1985

[54] DETERMINATION OF SULFUROUS ACID IN LIQUIDS AND AN APPARATUS THEREFOR

[75] Inventors: Katsuyoshi Ishii; Michio Kobori; Seiichi Morimoto, all of Nara, Japan

[73] Assignee: Sanwa Shoji Co., Ltd., Nara, Japan

[21] Appl. No.: 511,147

[22] Filed: Jul. 6, 1983

[30] Foreign Application Priority Data

Jul. 9, 1982 [JP] Japan .................... 57-120379

[51] Int. Cl.⁴ .................. G01N 33/00; G01N 33/16
[52] U.S. Cl. .................. 436/102; 73/863.01;
73/863.02; 222/56; 422/62; 422/68; 422/75;
436/43; 436/51; 436/55; 436/163
[58] Field of Search ............ 436/102, 121, 122, 101,
436/55, 163, 51, 100, 43; 422/62, 75-77, 68;
423/522, 539, 540; 137/391; 141/198, 199;
222/56, 64, 65; 73/863.01, 863.02, 863.81

[56] References Cited

U.S. PATENT DOCUMENTS

| | | | |
|---|---|---|---|
| 1,084,658 | 1/1914 | Pearson | 222/56 X |
| 3,117,954 | 1/1964 | Hupfer | 436/100 X |
| 3,660,035 | 5/1972 | Marsh | 422/75 |
| 3,717,435 | 2/1973 | Erty et al. | 422/75 |
| 3,870,466 | 3/1975 | Rellstab et al. | 422/75 X |
| 3,987,153 | 10/1976 | Stiles | 423/522 |
| 4,026,665 | 5/1977 | Mansfield et al. | 422/77 X |

FOREIGN PATENT DOCUMENTS 0628406 10/1978 U.S.S.R. .................. 222/64

OTHER PUBLICATIONS

Grant, *Hackh's Chemical Dictionary*, 1969, Frontispiece and p. 115.
"New Method for Determining Sulphur Dioxide in Wine", B. C. Rankine, Aust. Wine, Brew., Spirit Rev. vol. 80, pp. 14–15, (1962).
"Establishment of a Modified Rankine Method for the Separate Determination of Free and Combined Sulfites in Foods", by K. Fujita et al., published in Z. Lebensm. Unters. Forsch, vol. 168, pp. 206–211, (1979).

*Primary Examiner*—David L. Lacey
*Assistant Examiner*—Robert J. Hill, Jr.
*Attorney, Agent, or Firm*—Lyon & Lyon

[57] ABSTRACT

A method and an apparatus providing a simple and speedy determination of a slight amount of sulfurous acid contained in liquids by means of pH meters, based on the Modified Rankine's method in principle, and wherein the pH of a first sample of liquid is determined before and after adding an amount of hydrogen peroxide thereto, the pH of a second sample of liquid is determined before and after adding an amount of an acid or lower pH buffer solution thereto, and the concentration of sulfurous acid in the liquid is calculated from the measured pH values and an equation derived from the functional relationship:

$$c = f(\Delta pH_A, \Delta pH_B)$$

wherein c is the concentration of sulfurous acid.

4 Claims, 1 Drawing Figure

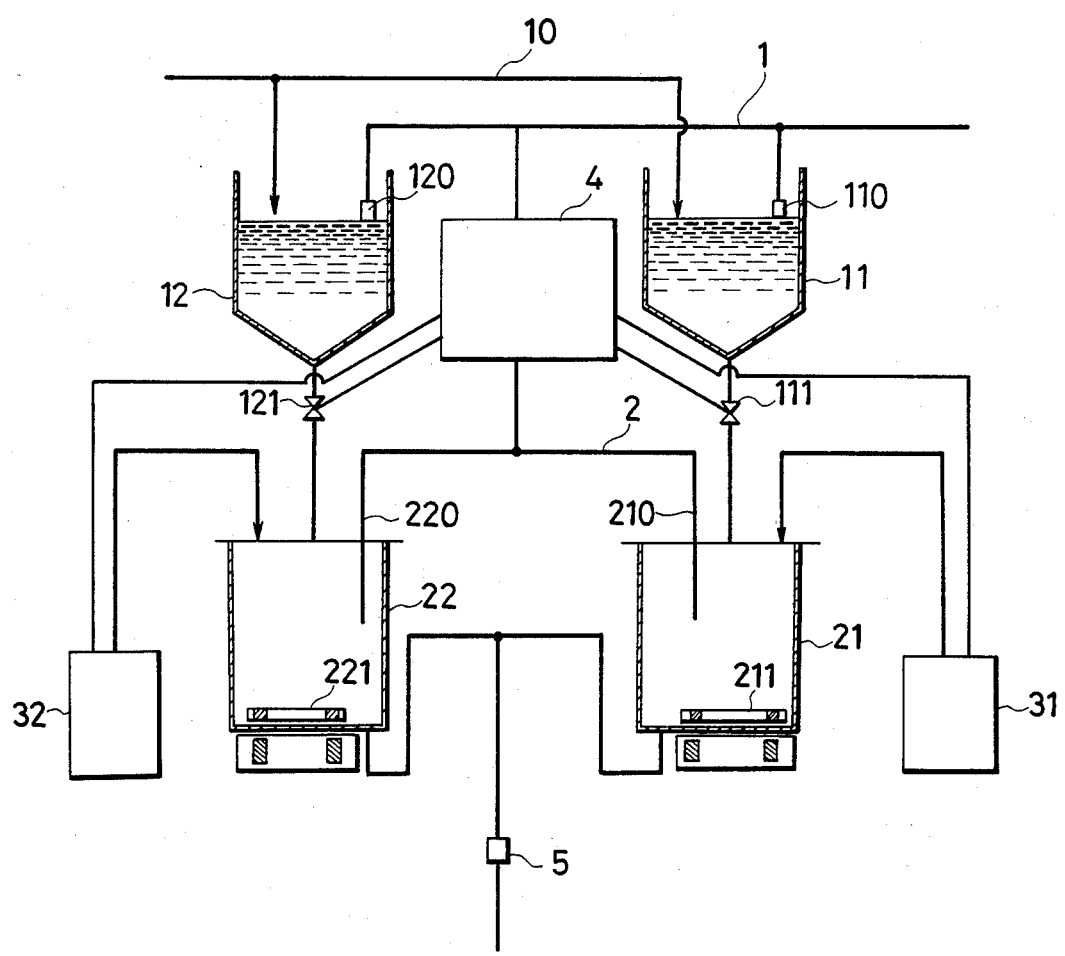

DETERMINATION OF SULFUROUS ACID IN LIQUIDS AND AN APPARATUS THEREFOR

BACKGROUND OF THE INVENTION

The present invention relates to a determination of sulfurous acid, especially a small amount of sulfurous acid, in liquids and an apparatus therefor. More particularly, the present invention relates to a novel, simple and speedy determination of sulfurous acid based on the Modified Rankine's method, which has been adopted in Japanese Health and Medical Laboratories, and an apparatus therefor.

Sulfurous acid and sulfites are generally used for foods as a bleaching or a discoloration inhibitor. They are employed in the production of cornstarch as an antiseptic and a stimulator for starch purification. They are also used for the sterilization of vessels, preservation of fresh fruit juices and regulation of fermentation processes in the production of wines. They are also employed in the fumigation of dry fruits.

A maximum amount of sulfurous acid and sulfites remaining in foods treated with sulfurous acid and sulfites is provided in the Japanese Food Hygiene Regulations in detail. For example, the amount of sulfurous acid or sulfites remaining in dried gourd shavings must be less than 5,000 ppm as sulfur dioxide, that in dried apricots and dried peaches less than 2,000 ppm, that in powdered Konnyaku (jellied extract from arum tree) less than 900 ppm, that in wines less than 350 ppm and that in general foods less than 30 ppm. Sulfurous acid and sulfites are prohibited for use with sesames, beans and vegetables.

Since people have taken an increasing interest in food sanitation, nowadays, the amount of and kinds of food additives have become severely limited. Food manufacturers must control the sulfurous acid content remaining in final products within a statutory standard when they use sulfurous acid or sulfites in the food manufacturing process. Thus, they are required to determine an amount of sulfurous acid remaining in foods and conduct process control.

For determination of a slight amount of sulfurous acid remaining in foods, the Modified Monnier-Williams method, the distilled iodine method, the Colorimetric method, the microdiffusion method, the Modified Rankine's Alkaline Titration method, the Modified Rankine's Colorimetric method, gas chromatography, etc. have been used. These methods require particular apparatus, a great deal of skill and a long period of time for determination of sulfurous acid. In addition, automatic determination cannot be adopted by these methods in principle.

SUMMARY OF THE INVENTION

This invention was established based on the knowledge that:
(i) when an amount of hydrogen peroxide is added in excess to a sample liquid, according to the principle of the Modified Rankine's method, the total amount of sulfurous acid in the sample liquid converts to sulfuric acid thereby decreasing the pH value of the sample liquid due to a difference in degree of dissociation between sulfurous acid and sulfuric acid;
(ii) The decrease of the pH value of the sample liquid is proportional to a first-order concentration of sulfurous acid;
(iii) There is a functional relationship between the proportion constant at the above (ii) and the buffer strength of the sample liquid; and
(iv) Thus, the following equation (1) can be set up:

$$c = f(\Delta pH_A, \Delta pH_B) \tag{1}$$

wherein
c is the concentration of sulfurous acid contained in said sample liquid,
$\Delta pH_A$ is the difference in pH value between the pre- and the post-addition of hydrogen peroxide to said sample liquid, and
$\Delta pH_B$ is the difference in pH value between the pre- and the post-addition of an acid or a lower pH buffer solution to said sample liquid.

The method of this invention which overcomes the above-discussed disadvantages of the prior art, comprises:
(a) measuring the pH value of a sample liquid containing sulfurous acid,
(b) adding hydrogen peroxide in excess to said sample liquid and measuring the pH value of said sample liquid containing hydrogen peroxide,
(c) adding a certain amount of an acid or a lower pH buffer solution to the same sample liquid as in process (a) and measuring the pH value of said sample liquid containing the acid or the lower pH buffer solution,
(d) calculating the following equation (1) based on the above-measured pH values:

$$c = f(\Delta pH_A, \Delta pH_B) \tag{1}$$

wherein
c is the concentration of sulfurous acid contained in said sample liquid,
$\Delta pH_A$ is the difference in pH value between the pre- and the post-addition of hydrogen peroxide to said sample liquid, and
$\Delta pH_B$ is the difference in pH value between the pre- and the post-addition of an acid or a lower pH buffer solution to said sample liquid.

The apparatus of this invention which also overcomes the above-discussed disadvantages of the prior art, comprises:
(a) a pair of measuring means for measuring a certain amount of a sample liquid,
(b) a pair of pH-measuring means, which are connected to said sample liquid-measuring means by means of values, containing said measured sample liquid,
(c) a pair of automatic burettes connected to said pH-measuring means; one of said burettes adding an amount of hydrogen peroxide to one of said sample liquids in one of said pH-measuring means and the other burette adding an amount of an acid or a lower pH buffer solution to the other sample liquid in the other pH-measuring means,
(d) a calculating means for calculation of the following equation (1) based on the pH values measured by said pH-measuring means with regard to the pre- and the post-addition of hydrogen peroxide and an acid or a lower pH buffer solution to said sample liquid:

$$c = f(\Delta pH_A, \Delta pH_B) \tag{1}$$

wherein
c is the concentration of sulfurous acid contained in said sample liquid, $\Delta pH_A$ is the difference in pH value between the pre- and the post-addition of hydrogen peroxide to said sample liquid, and $\Delta pH_B$ is the difference in pH value between the pre- and the post-addition of an acid or a lower pH buffer solution to said sample liquid.

The pair of measuring means comprise a measuring vessel and a level detector, respectively, connected to a sampling tube.

The pair of pH measuring means comprise a pH measuring vessel and a pH meter connected to the pH measuring vessel, respectively.

Thus, the invention described herein makes possible the objects of; (a) providing a simple and speedy determination of a slight amount of sulfurous acid contained in a sample liquid by means of pH meters alone; (b) providing an apparatus for determining simply and speedily a slight amount of sulfurous acid in a sample liquid by means of pH meters alone; (c) providing an apparatus for automatically determing simply and speedily sulfurous acid in a sample liquid by means of electric signals from pH meters; and (d) providing an apparatus for automatically controlling processes based on data of sulfurous acid.

BRIEF DESCRIPTION OF THE DRAWINGS

This invention may be better understood and its numerous objects and advantages will become apparent to those skilled in the art by reference to the accompanying drawing as follows:

The FIGURE is an illustration of an apparatus in accordance with this invention.

DESCRIPTION OF THE PREFERRED EMBODIMENTS

The method of this invention is based on the Modified Rankine's Alkaline Titration method in principle, in which hydrogen peroxide is added to a sample liquid to convert the total amount of sulfurous acid in the sample liquid into sulfuric acid. The difference in degree of dissociation between sulfurous acid and sulfuric acid, results in a lowering of the pH value of the sample liquid. It has been confirmed by the experimental results that the lowering of the pH value of the sample liquid is proportional to a first-order concentration of sulfurous acid as represented by the following equation (2) or (2'):

$$SO_2 \text{ concentration} = K(\Delta pH_A) + f(K) \qquad (2)$$

$$SO_2 \text{ concentration} = K(\Delta pH_A) + k \qquad (2')$$

wherein

K and k are a proportion constant, respectively;

$\Delta pH_A$ is the difference in pH value between the pre- and the post-addition of hydrogen peroxide to the sample liquid; and f(K) is a function of K.

It has been confirmed by the experimental results that there is a functional relationship between the above-mentioned constant K and the buffer strength of the sample liquid, which is represented by the following equation (3):

$$K = g(\Delta pH_B) \qquad (3)$$

wherein $\Delta pH_B$ is the buffer strength of the sample liquid.

The "buffer strength" or "$\Delta pH_B$" means the degree of lowering of the pH value at the time when a certain amount of an acid or a lower pH buffer solution is added to the sample liquid.

In light of the equations (2) and (3), the afore-mentioned equation (1) is represented by the following equation (4):

$$c = \{g(\Delta pH_B)\} \times (\Delta pH_A) + f\{g(\Delta pH_B)\} \qquad (4)$$

In light of the equations (2') and (3), the afore-mentioned equation (1) is represented by the following equation (4') as well:

$$c = \{g(\Delta pH_B)\} \times (\Delta pH_A) + k \qquad (4')$$

wherein c is the concentration of sulfurous acid;

$\Delta pH_A$ is the difference in pH value between the pre- and the post-addition of hydrogen peroxide to the sample liquid;

$\Delta pH_B$ is the difference in pH value between the pre- and the post-addition of an acid or a lower buffer solution to the sample liquid; and k is a constant.

It is to be assumed that the above equation (4) and (4') are an example of the afore-mentioned equation (1). It is to be also assumed that equations, other than the aforementioned equations (4) and (4'), suitable for sample liquids to be measured may be derived from the equation (1).

According to this invention, the determination of sulfurous acid is carried out using the equation (1) as follows:

First, the pH value of a sample liquid is measured thereby obtaining a data for $pH_1$. Then, a large excess of hydrogen peroxide is added to the sample liquid, followed by measurement of its pH value thereby obtaining a data for $pH_2$. The difference between the data $pH_1$ and the data $pH_2$ is represented as $\Delta pH_A$.

To another portion of the sample liquid, a certain amount of an acid or a lower pH buffer solution is added followed by measurement of its pH value thereby obtaining a data for $pH_3$. The difference between the data $pH_1$ and the data $pH_3$ is represented as $\Delta pH_B$. Since the value of $\Delta pH_B$ includes the buffer strength of the sample liquid, the acid or the lower pH buffer solution to be applied in order to determine the buffer strength of the sample liquid is not limited to a particular kind. For example, sulfuric acid, hydrochloric acid, a variety of organic acids or the like may be used. An example of a lower pH buffer solution is oxalic acid-oxalate buffer solution.

Using $\Delta pH_A$ and $\Delta pH_B$, the afore-mentioned equation (1) is calculated to determine the amount of sulfurous acid in the sample liquid.

In calculating the above-mentioned equation (1) to determine the content of sulfurous acid in a liquid, an experimental formula is set up, in advance, using the least squares method, from the values of $\Delta pH_A$ and $\Delta pH_B$ with regard to a variety of sample liquids, which comprise an individual sulfurous acid-content and a buffer strength, and the value of sulfurous acid-content determined by the Modified Rankine's Alkaline Titration method with regard to the sample slurry. For example, when a sample liquid is a cornstarch liquid, the above-mentioned equation (4) is adopted which is represented as the following equation (5):

$$c = \{77.4 + 194.9 \times 0.769^{(25 \times \Delta pH_B - 6)}\} \times (\Delta pH_A + 0.04) \tag{5}$$

On the other hand, the Modified Rankine's method and the conventional methods of determination of sulfurous acid are required for an accurate weighing of the sample, a heating and distillation of the sample, a nitrogen gas ventilation, a titration, a colorimetry, etc., which are troublesome and labor consuming and require particular apparatuses.

The apparatus according to this invention is an apparatus which can be set up to conduct an automatic sampling of a liquid flowing continuously in processes to carry out an automatic determination of sulfurous acid contained therein. The apparatus conducts an automatic process control based on the data of the sulfurous acid concentration which are determined by a calculation means in the apparatus. The pH-measuring means in the apparatus of this invention is not required to accurately indicate an absolute value of pH, but is required to accurately indicate a difference of the pH values.

EXAMPLE 1

As a sample liquid containing sulfurous acid, a cornstarch slurry was employed which is a starch separated and purified from corn. The first step of the cornstarch production is to soak corn grains in water containing sulfurous acid. The aqueous solution of sulfurous acid is used as an antiseptic and a stimulator for starch purification. For this purpose, the use of a high concentration of sulfurous acid is effective. However, the amount of sulfurous acid remaining in the final product, cornstarch, must be less than 30 ppm in light of the Japanese Food Hygiene Regulations.

The sample liquid used in Example 1 is a cornstarch slurry picked up at a step preceding the final step of dehydration and drying. The analytical values of the sample liquid are shown in Table 1.

TABLE 1

| pH | 4.01 |
|---|---|
| Sulfurous acid concentration (By Modified Rankine's Titration) | 24 ppm |

Two hundred ml each of the sample liquid were placed in the vessels A and B. To the vessel A, 2 ml of 30% hydrogen peroxide was added with stirring. The pH value of the mixture in the vessel A was measured as 3.94 by a pH meter. Thus, $\Delta pH_A = 4.01 - 3.94 = 0.07$. To the vessel B, 2 ml of 0.1N sulfuric acid was added with stirring. The pH value of the mixture in the vessel B was 3.73. Thus, $\Delta pH_B = 4.01 - 3.73 = 0.28$. Substituting the above values for $\Delta pH_A$ and $\Delta pH_B$ in the above-mentioned experimental formula (5), the concentration of sulfurous acid was calculated to be 25 ppm.

Namely, the concentration of sulfurous acid $$= \{77.4 + 194.9 \times 0.769^{(25 \times \Delta pH_B - 6)}\} \times (\Delta pH_A + 0.04) \tag{5}$$

$$= 25 \text{ ppm}$$

The pH value 25 ppm calculated according to this invention's method is nearly equal to the pH value 24 ppm obtained by the Modified Rankine's Alkaline Titration method.

EXAMPLE 2

Eighteen kinds of cornstarch slurries, which contain sulfurous acid ranging from 4 ppm to 127 ppm, were subjected to the determination of sulfurous acid as carried out in Example 1. The data are shown in Table 2.

TABLE 2

| | | | | | | | | | |
|---|---|---|---|---|---|---|---|---|---|
| Invention's Method | 23 | 15 | 10 | 3 | 57 | 20 | 15 | 8 | 4 |
| Modified Rankine's Method | 23 | 14 | 8 | 2 | 58 | 22 | 16 | 7 | 2 |
| Invention's Method | 89 | 21 | 20 | 13 | 6 | 127 | 34 | 26 | 20 |
| Modified Rankine's Method | 87 | 23 | 20 | 11 | 4 | 125 | 33 | 25 | 17 |

All of the data obtained by the invention's method are nearly equal to those of the Modified Rankine's method.

EXAMPLE 3

Dried gourd shavings were used as a sample. Ten grams of commercially available dried gourd shavings were sliced and placed in a triangular flask. To this flask, 300 ml of distilled water was added. The flask was shaken for 1 hour. The mixture was filtered with a filter paper, the residue on which was pressed by a glass bar. To the residue on the filter and in the flask, 300 ml of distilled water was added. The mixture was well shaken and filtered. An additional amount of distilled water was added to the filtrate to give a total amount of 600 ml.

The resulting filtrate was subjected to a determination of $\Delta pH_A$ and $\Delta pH_B$ as carried out in Example 1, thereby obtaining that $\Delta pH_A$ was 0.05 and $\Delta pH_B$ was 0.40. Substituting the above data for $\Delta pH_A$ and $\Delta pH_B$ in the below-mentioned experimental formula (6) yields 27 ppm of sulfurous acid:

$$\text{SO}_2 \text{ concentration (ppm)} = 1836 \times 0.0143^{(\Delta pH_B)} \times (\Delta pH_A + 0.03) \tag{6}$$

This experimental formula was derived, using the least squares method, based on the data of sulfurous acid-content measured by the Modified Rankine's method and the data of $\Delta pH_A$ and $\Delta pH_B$ obtained according to this invention with respect to the amount of dried gourd shavings, as in the afore-mentioned of experimental formula (5) with respect to the amount cornstarch slurries. Thus, the sulfurous acid-content in 1 g of the dried gourd shavings is calculated to be $(27 \times (600/10) =)$ 1,620 ppm.

On the other hand, the content of sulfurous acid in the above-mentioned filtrate was measured to be 26 ppm by the Modified Rankine's method. Measuring the sulfurous acid-content in 1 g of the dried gourd shavings by the Modified Rankine's method, the data of 1,590 ppm were obtained. Both of those data are nearly equal.

EXAMPLE 4

The FIGURE shows an apparatus of this invention which comprises a pair of measuring means 1 connected to a sampling tube 10, and a pair of pH measuring means 2. The measuring means 1, which serve to measure a certain amount of the sample liquid, comprise the vessels 11, 12 and the level dectectors 110, 120. The pair of pH measuring means 2, which serve to measure the pH value of the sample liquid, comprise the pH measuring vessels 21 and 22, respectively, and the pH meters 210 and 220, respectively. The pH meter 210 connects to the pH measuring vessel 21 which is connected to the measuring vessel 11 through a valve 111. The pH meter 220 connects to the pH measuring vessel 22 which is connected to the measuring vessel 12 through a valve 121.

An automatic burette 31 is connected to the pH measuring vessel 21 and an automatic burette 32 is connected to the pH measuring vessel 22. From one of those burrettes, a certain amount of hydrogen peroxide having a given concentration is added to one of those pH measuring vessels, and from the other burette a certain amount of sulfuric acid having a given concentration is added to the other pH measuring vessel. The pH measuring means 2 are connected to a calculation means 4, which calculates a concentration of sulfurous acid in the sample liquid by the afore-mentioned equation (1) based on the pH value of the sample liquid prior to and after the addition of hydrogen peroxide and sulfuric acid, respectively, by means of the automatic burette 31 or 32 to the pH measuring vessel 21 or 22. Since the sample liquid, which is a portion of liquid flowing continuously in processes, is continuously fed to the vessels, the calculation means 4 can conduct a process control according to the calculated pH value.

The pH measuring vessels 21, 22 are connected to an aspirator 5, which eliminates the used sample liquid in these vessels each time a pH measurement has been completed and washes the inside of the vessels with water and then excludes the water therefrom to prepare the vessels for the next cycle of the pH measurement.

In cornstarch factories, a purified cornstarch slurry is generally pipe-transported to a dehydration and drying process. The cornstarch slurry is branched to the sampling tube 10 through which the sample liquid is fed to the measuring vessels 11 and 12, respectively. The level detectors 110 and 120, which are mounted in the measuring vessels 11 and 12, respectively, operate to feed 200 ml of the sample liquid into each of the vessels 11 and 12 in absolute accuracy. Upon measurement, the valves 111 and 121 are open and the sample liquid in each vessel 11, 12 is placed in the pH measuring vessels 21 and 22, respectively, in which the pH value of each sample liquid is measured by the pH meters 210 and 220, respectively, with stirring by means of the stirring means 211, 221. The measured pH values, both of which were 4.08, are recorded by the calculating means 4. From the burette 31, then, exactly 2 ml of 30% hydrogen peroxide was added to the vessel 21. The pH meter 210 stabilized over 2 minutes, after which it indicated 3.92 of the pH value which was recorded by the calculation means 4. From the burette 32, likewise, exactly 2 ml of 0.1N sulfuric acid was added to the vessel 22. The pH meter 220 indicated 3.59 of the pH value which was recorded by the calculation means 4.

The calculation means 4 calculated the difference ($\Delta pH_A = 0.16$) in pH between the pre- and the post-addition of hydrogen peroxide to the vessel 21 and the difference ($\Delta pH_B = 0.49$) in pH between the pre- and the post-addition of sulfuric acid to the vessel 22, and then substituted those data for $\Delta pH_A$ and $\Delta pH_B$ in the afore-mentioned experimental formula (5), which has been derived in advance with respect to the cornstarch slurry, thereby obtaining 23 ppm of the concentration of sulfurous acid.

Sulfurous acid concentration (ppm) = (5)

$$\{77.4 + 194.9 \times 0.769^{(25 \times \Delta pH_B - 6)}\} \times (\Delta pH_A + 0.04) = 23 \text{ ppm}$$

According to the Modified Rankine's method, the concentration of sulfurous acid contained in said sample liquid was determined to be 22 ppm.

After the determination of the content of sulfurous acid in the sample liquid was completed, the aspirator 5 eliminated the liquid in the vessels 21 and 22 and washed the vessels with water and then excluded the water from the inside of the vessels to prepare the vessels for the next cycle of the pH measurement. The sequence of this operation is also carried out by the calculation means 4, which is able to order a process control, e.g. a change of the amount of washing water.

We claim:

1. A method for the determination of sulfurous acid in a liquid, comprising:
    (a) measuring the pH value of a first sample of a liquid containing sulfurous acid,
    (b) adding to said first sample of liquid an excess of hydrogen peroxide to convert said sulfurous acid to sulfuric acid, and measuring the pH value of said first sample of liquid containing hydrogen peroxide,
    (c) adding a predetermined amount of an acid or a lower pH buffer solution to a second sample of said liquid containing sulfurous acid and measuring the pH value of said second sample of said liquid containing the acid or the lower pH buffer solution, and
    (d) calculating the concentration of sulfurous acid in said liquid based on the above-measured pH values and an equation derived from the functional relationship:

$$c = f(\Delta pH_A, \Delta pH_B)$$

wherein c is the concentration of sulfurous acid contained in said sample liquid, $\Delta pH_A$ is the difference in pH value between the pre- and the post-addition of hydrogen peroxide to said first sample of said liquid, and $\Delta pH_B$ is the difference in pH value between the pre- and the post-addition of an acid or a lower pH buffer solution to said second sample of said liquid.

2. An apparatus for determining the concentration of sulfurous acid in a liquid comprising:
    (a) first and second measuring means for collecting predetermined amounts of a liquid containing sulfurous acid and generating first and second signals, respectively, when said first and second measuring means contain said predetermined amounts,
    (b) first and second normally closed control valves operatively connected to said first and second measuring means, respectively, for dispensing liquid from said first and second measuring means,
    (c) first and second pH-measuring means operatively connected to said first and second control valves, respectively, for receiving liquid from said first and second measuring means, respectively,
    (d) first and second automatic burette means operatively connected to said first and second pH-measuring means, respectively,
    (e) control means operatively connected to said first and second measuring means, said first and second control valves, said first and second pH-measuring means and said first and second automatic burette means, said control means having an operative mode wherein it receives said first and second signals and in response thereto generates third and fourth signals to open said first and second control valves, respectively, and dispense predetermined amounts of a liquid containing sulfurous acid from said first and second measuring means to said first and second pH-measuring means, respectively, to obtain first and second samples therein, said control means then generates fifth and sixth signals to activate said first and second pH-measuring means, respectively, to measure the pH of said first and second samples and generate seventh and eighth respective signals representative thereof, said control means receives and records said seventh and eighth signals and then generates a ninth signal to activate said first automatic burette means to add a predetermined amount of hydrogen peroxide to said first sample in said first measuring means, a tenth signal to activate said second automatic burette means to add a predetermined amount of an acid or low pH buffer solution to the second sample in said second pH-measuring means, and an eleventh and twelfth signal to activate said first and second pH measuring means after the addition of hydrogen peroxide, acid or low pH buffer solution to measure the pH of said first and second samples and generate thirteenth and fourteenth respective signals representative thereof, said control means receives and records said thirteenth and fourteenth signals and then calculates and displays the concentration of sulfurous acid in said liquid by an equation based on the functional relationship:

$$c = f(\Delta pH_A, \Delta pH_B)$$

wherein c is the concentration of sulfurous acid in said liquid, $\Delta pH_A$ is a value corresponding to a difference between said seventh and thirteenth signals, and $\Delta pH_B$ is a value corresponding to a difference between said eighth and fourteenth signals.

3. An apparatus according to claim 2, wherein each measuring means comprises a measuring vessel operatively connected to a level detector and a sampling tube.

4. An apparatus according to claim 2, wherein each pH-measuring means comprises a pH measuring vessel and a pH meter operatively connected thereto.

* * * * *